(12) United States Patent
Tsai et al.

(10) Patent No.: US 9,404,128 B2
(45) Date of Patent: Aug. 2, 2016

(54) PROCESSES FOR THE ACIDIC, ANAEROBIC CONVERSION OF HYDROGEN AND CARBON OXIDES TO OXYGENATED ORGANIC COMPOUND

(71) Applicants: Shih-Perng Tsai, Naperville, IL (US); Robert Hickey, Okemos, MI (US); Jianxin Du, Naperville, IL (US); Jian Xu, Naperville, IL (US); Joshua Schumacher, Warrenville, IL (US)

(72) Inventors: Shih-Perng Tsai, Naperville, IL (US); Robert Hickey, Okemos, MI (US); Jianxin Du, Naperville, IL (US); Jian Xu, Naperville, IL (US); Joshua Schumacher, Warrenville, IL (US)

(73) Assignee: SYNATA BIO, INC., Warrenville, IL (US)

( * ) Notice: Subject to any disclaimer, the term of this patent is extended or adjusted under 35 U.S.C. 154(b) by 81 days.

(21) Appl. No.: 14/536,413

(22) Filed: Nov. 7, 2014

(65) Prior Publication Data

US 2016/0130610 A1 May 12, 2016

(51) Int. Cl.
*C12P 7/06* (2006.01)
(52) U.S. Cl.
CPC ..................... *C12P 7/065* (2013.01)

(58) Field of Classification Search
None
See application file for complete search history.

(56) References Cited

U.S. PATENT DOCUMENTS

| | | | | |
|---|---|---|---|---|
| 8,535,919 B2 * | 9/2013 | Hickey | ...................... | C12N 1/20 435/140 |
| 8,597,934 B2 * | 12/2013 | Tobey | ...................... | C12P 7/04 435/140 |
| 8,936,927 B2 * | 1/2015 | Hickey | ...................... | C12P 7/06 435/245 |
| 9,157,100 B2 * | 10/2015 | Hickey | ...................... | C12P 5/023 |
| 9,181,565 B2 * | 11/2015 | Tobey | ................... | C12M 21/00 |
| 2013/0078688 A1 * | 3/2013 | Hickey | ...................... | C12P 7/00 435/140 |
| 2015/0132810 A1 * | 5/2015 | Hickey | ...................... | C12P 7/06 435/132 |

FOREIGN PATENT DOCUMENTS

WO    WO 2011/139163    * 11/2011    ................ C12P 7/06

\* cited by examiner

*Primary Examiner* — Allison Fox
(74) *Attorney, Agent, or Firm* — Cardinal Law Group

(57) ABSTRACT

Processes for the bioconversion of syngas to oxygenated organic compound are disclosed that reliably, cost-effectively and efficiently supply sulfur nutrient to microorganisms contained in acidic, aqueous fermentation menstrua. In the processes of this invention, basic, aqueous solution used to maintain the pH of the aqueous fermentation menstruum is used to remove hydrogen sulfide from the off-gas from the fermentation menstruum for recycle to the fermentation menstruum.

15 Claims, 1 Drawing Sheet

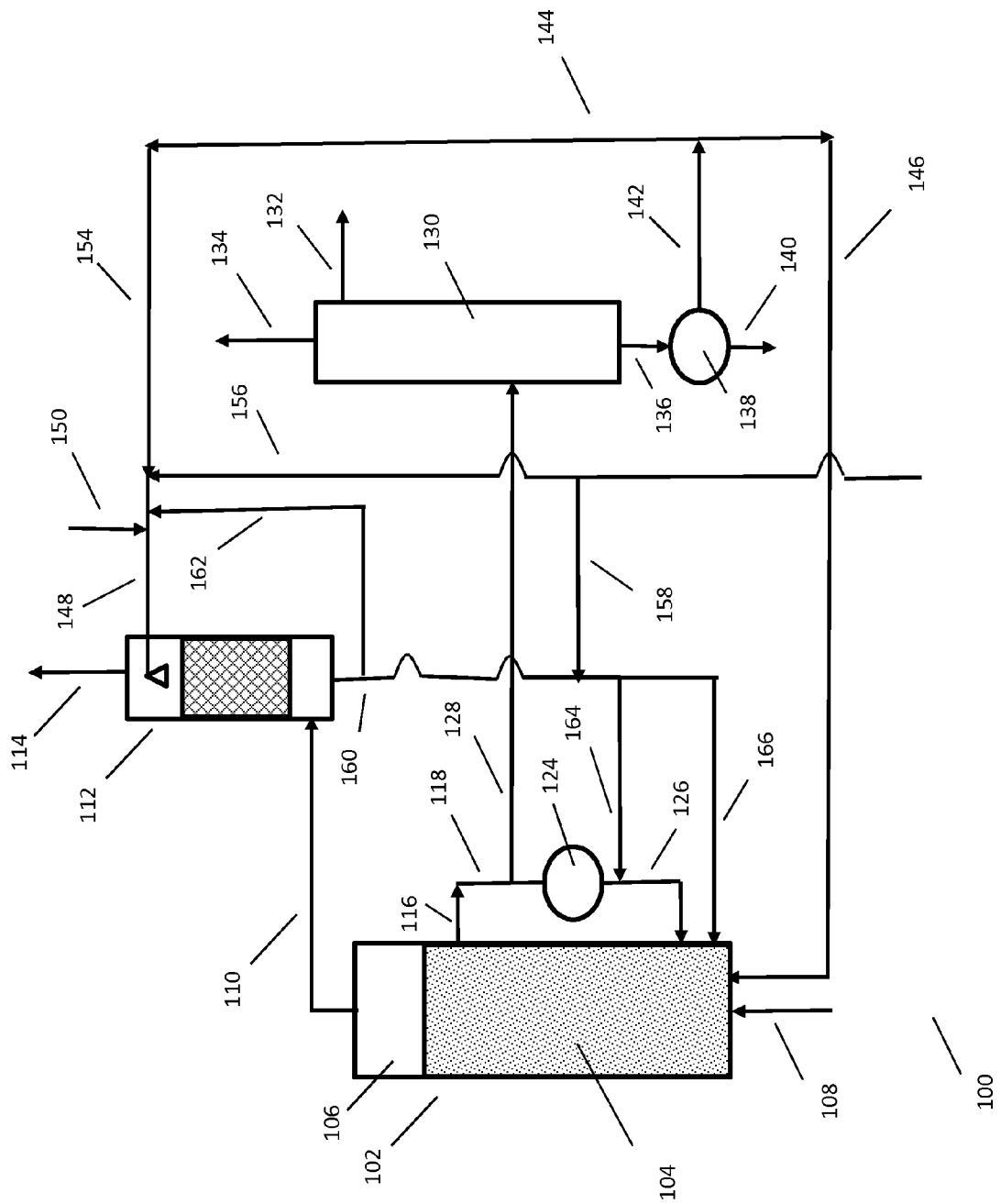

PROCESSES FOR THE ACIDIC, ANAEROBIC CONVERSION OF HYDROGEN AND CARBON OXIDES TO OXYGENATED ORGANIC COMPOUND

FIELD OF THE INVENTION

This invention pertains to processes for the anaerobic bioconversion of hydrogen and carbon oxides to oxygenated organic compound wherein a basic, aqueous solution used for control of the pH of the fermentation menstruum is used to recover and recycle hydrogen sulfide from the off-gas from the bioconversion.

BACKGROUND

Anaerobic fermentations of hydrogen and carbon monoxide involve the contact of a gaseous substrate-containing feed with an aqueous fermentation menstruum containing microorganisms capable of generating oxygenated organic compounds such as ethanol, acetic acid, propanol and n-butanol. The bioconversion of carbon monoxide results in the production of oxygenated organic compound and carbon dioxide. The conversion of hydrogen involves the consumption of hydrogen and carbon dioxide, and this conversion is sometimes referred to as the $H_2/CO_2$ conversion or, as used herein, the hydrogen conversion.

Sulfur is a key nutritional need of anaerobic microorganisms used in these fermentations to produce oxygenated organic compound. Organic sulfur sources, such as cysteine, have been used to provide the nutritional sulfur. These organic sulfur sources are expensive, and alternative sources of sulfur to meet this nutritional need have been sought. Less expensive sources of sulfur include, but are not limited to, hydrogen sulfide, and sulfite, bisulfite, thiosulfate and metabisulfite anions. However, typical aqueous menstrua for the bioconversion of carbon monoxide and of hydrogen and carbon dioxide are acidic. Consequently the equilibrium for hydrogen sulfide, which provides the sulfhydryl anion that is believed to be used by the microorganisms, strongly favors gaseous hydrogen sulfide as opposed to the sulfhydryl anion, and gaseous hydrogen sulfide rapidly exits the aqueous menstruum.

To maintain available sulfur nutrient in view of the evolution of hydrogen sulfide from the aqueous menstruum, the sulfur nutrient is typically added in an amount much greater than that metabolically required. This overdosing increases operating costs due to the amount of sulfur nutrient required to be supplied. In addition, the off-gas contains hydrogen sulfide in problematic concentrations. Hence, accommodations may be required to remove or reduce the concentration of hydrogen sulfide in the off-gas to enable the use or disposal of the off-gas and to attenuate corrosive properties of the off-gas.

Accordingly, processes for the anaerobic conversion of carbon monoxide and of hydrogen and carbon dioxide to oxygenated organic compounds are sought that can reduce the amount of sulfur nutrient required to be supplied to the aqueous menstruum and attenuate the concentration of hydrogen sulfide in the off-gas.

SUMMARY

By this invention processes are provided for the bioconversion of syngas to oxygenated organic compound which efficiently use sulfur nutrient. In accordance with the processes of this invention, a basic, aqueous stream which is required to maintain the pH of the fermentation menstruum for the bioconversion, is used to recover hydrogen sulfide from the off-gas from the bioconversion. Hence, the processes are particularly advantageous for commercial-scale units where overall production costs are important. By recovering hydrogen sulfide from the off-gas for recycle to the fermentation menstruum, the amount of fresh sulfur nutrient required to be supplied can be reduced. Moreover, the hydrogen sulfide concentration of the off-gas can, if desired, be reduced to levels where the off-gas can be combusted without the need for further sulfur removal to meet environmental regulations.

Since hydrogen sulfide is recovered and recycled, additional advantages occur. For instance, higher partial pressures of hydrogen sulfide can be economically maintained thereby increasing the concentration of sulfhydryl anion in the fermentation menstruum. Lower pH fermentation menstrua, which may be more favorable to the bioconversion but reduce the sulfhydryl anion concentration in the menstrua, can be more economically attractive. Also, although any suitable, fresh sulfur nutrient can be used, the ability to recover and recycle hydrogen sulfide enables the use of hydrogen sulfide or compounds that readily generate hydrogen sulfide when introduced into the fermentation menstruum as opposed to more expensive sulfur nutrients such as cysteine.

In a broad aspect, this invention pertains to continuous processes for the anaerobic bioconversion of a gas substrate comprising carbon monoxide, hydrogen and carbon dioxide in an aqueous menstruum containing microorganisms suitable for converting said substrate to oxygenated organic compound, which processes comprise:

a. continuously contacting said gas substrate with said aqueous menstruum under acidic, anaerobic fermentation conditions including the presence of sulfur nutrient to bioconvert gas substrate to oxygenated organic compound and provide an oxygenated organic compound-containing menstruum and a depleted gas phase containing hydrogen sulfide;

b. continuously or intermittently introducing into said aqueous menstruum a basic, aqueous solution in an amount sufficient to maintain the aqueous menstruum above a pH that unduly adversely affects the microorganisms, preferably above a pH of about 4, say, above a pH of about 4.5;

c. continuously or intermittently withdrawing a portion of said menstruum for recovery of said oxygenated organic compound, said withdrawal being sufficient to maintain the oxygenated organic compound in said menstruum below a concentration that unduly adversely affects the microorganisms;

d. continuously withdrawing the depleted gas phase from said aqueous menstruum; and e. continuously contacting at least a portion, preferably substantially all, of the depleted gas phase withdrawn from said aqueous menstruum with at least a portion of the basic, aqueous solution prior to its introduction into said aqueous menstruum in step (b) to reduce the concentration of hydrogen sulfide in the depleted gas phase whereby the basic, aqueous solution contains sulfhydryl anion.

From the standpoint of economics although any organic or inorganic base may be used, the basic, aqueous solution comprises a caustic solution, i.e., containing one or more of sodium hydroxide, potassium hydroxide and calcium oxide. Often the pH of the basic, aqueous solution contacting the depleted gas phase is in the range of 7.5 to about 14, preferably, about 8.0 to 9. The basic, aqueous solution may be obtained from any suitable source. Generally, the basic, aqueous solution is procured as an aqueous solution or is formulated at the site from procured solid or concentrated aqueous base. The basic, aqueous solution may be prepared or diluted with one or more of makeup water for the fermentation or water obtainable from the process such as withdrawn aqueous fermentation menstruum or still bottoms where the recovery of the oxygenated organic compound is by distillation.

A basic, aqueous solution can also remove other acid gases, such as carbon dioxide, from the depleted gas phase. In some instance, for instance, those where the substrate is hydrogen-rich, the recovered carbon dioxide can be used for the hydrogen/carbon dioxide conversion to oxygenated organic compound. Where the substrate is hydrogen lean, recycled carbon dioxide is of little benefit. In these instances, it may be desired to use a basic, aqueous solution that is ladened with carbonate and bicarbonate anions such that the sorption of carbon dioxide is attenuated.

In some preferred processes the concentration of hydrogen sulfide in the depleted gas after step (e) (herein referred to as treated substrate depleted gas is less than about 150, say, less than 100, and frequently between about 1 and 100, ppm by volume.

BRIEF DESCRIPTION OF THE DRAWINGS

FIG. 1 is a schematic depiction of an apparatus that can be used in the practice of the processes of this invention.

DETAILED DISCUSSION

All patents, published patent applications, unpublished patent applications and articles referenced herein are hereby incorporated by reference in their entirety.

Definitions

As used herein, the following terms have the meanings set forth below unless otherwise stated or clear from the context of their use.

The use of the terms "a" and "an" is intended to include one or more of the element described.

Oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous menstruum.

A bioreactor assembly is an assembly of one or more vessels suitable to contain aqueous menstruum and microorganisms for the bioconversion and can contain associated equipment such as injectors, recycle loops, agitators, and the like.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as garbage and municipal waste. Biomass does not include fossil fuels such as coal, natural gas, and petroleum.

Electron to carbon ratio is calculated as the quotient of the quantity of two times the sum of the molar concentrations of carbon monoxide and hydrogen divided by quantity of the sum of the molar concentrations of carbon monoxide and carbon dioxide:

$$e^-/C=([CO]+[H_2])/([CO]+[CO_2]).$$

The abbreviation ppm means parts per million. Unless otherwise stated or clear from the context, ppm is on a mass basis (ppm (mass)) for solids in a liquid medium and on a volume basis (ppmv) in gases based on the temperature and pressure of the gas.

Fossil carbonaceous materials, or fossil fuels, include, but are not limited to, natural gas; petroleum including carbonaceous streams from the refining or other processing of petroleum including, but not limited to, petroleum coke; and lignite and coal.

Aqueous menstruum, or aqueous fermentation menstruum, means a liquid water phase which may contain dissolved compounds including, but not limited to hydrogen, carbon monoxide, and carbon dioxide.

Intermittently means from time to time and may be at regular or irregular time intervals.

A concentration of the oxygenated organic compound below that which unduly adversely affects the rate of growth of the culture of microorganisms will depend upon the type of microorganism and the oxygenated organic compound. An unduly adverse effect on the growth rate means that a significant, usually at least a 20 percent, decrease in the growth rate of the microorganisms is observed in comparison to the growth rate observed in an aqueous menstruum having about 1.0 gram per liter oxygenated organic compound therein, all other parameters being substantially the same.

Deep tank bioreactor is a bioreactor having a depth of at least about 10 meters and can be operated to provide a substantial non-uniform substrate composition over the depth of the aqueous menstruum contained in the bioreactor. The term bubble column bioreactor as used herein refers to a deep tank bubble column bioreactor unless otherwise explicitly stated and include deep tank reactors where the gas is introduced as small bubbles to promote mixing. A commercial scale bioreactor has a capacity for aqueous menstruum of at least 1 million, and more preferably at least about 5, say, about 5 to 25 million, liters.

Substrate is one or more of (i) carbon monoxide and (ii) carbon dioxide and hydrogen. A feed gas contains substrate and may contain other components including, but not limited to, recycled off-gas or a fraction thereof and other additives, inerts such as methane and nitrogen, and other components that can be contained in a syngas.

Syngas means a gas, regardless of source, containing at least one of hydrogen and carbon monoxide and may, and usually does, contain carbon dioxide.

Syntrophic refers to the association of two or more different types (e.g. organisms, populations, strains, species, genera, families, etc.) of anaerobic microorganisms which are capable of forming a tightly associated metabolic relationship.

Co-culture of microorganisms refers to joint incubation or incubation together, of the syntrophic microorganisms. In the context of the present invention, the co-culture does not require cellular population growth during the joint incubation of the syntrophic microorganisms.

A syntrophic C3-producing microorganism is a microorganism capable of growing on ethanol and/or acetate as its primary carbon source to produce oxygenated organic compounds having three carbon atoms.

A syntrophic C4-producing microorganism is a butyrogen capable of growing on acetogenic oxygenated organic compounds as its primary carbon source. Butyrogens are any microorganism capable of converting syngas intermediates, such as ethanol and acetate and some hydrogen, to primarily n-butyrate. Butyrogens use at least one of two distinct pathways for butyrate production—the Butyryl CoA Acetyl Transferase pathway (BuCoAAT) and the Butyryl Kinase (BuK) pathway. The BuCoAAT pathway converts butyryl CoA to butyrate through the BuCoAAT enzyme while the BuK pathway converts butyryl CoA through a BuK enzyme.

Substrate and Feed Gas

Anaerobic fermentation to produce oxygenated organic compound uses a substrate comprising at least one of (i) carbon monoxide and (ii) carbon dioxide and hydrogen, the latter being for the hydrogen conversion pathway. The feed gas will typically contain nitrogen and methane in addition to carbon monoxide and hydrogen. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas.

Syngas is typically produced by a gasifier, reformer (steam, autothermal or partial oxidation). Any of the aforementioned biomass sources are suitable for producing syngas. The syngas produced thereby will typically contain from 10 to 60 mole % CO, from 10 to 25 mole % $CO_2$ and from 10 to 75, often at least about 30, and preferably between about 35 and 65, mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing and from industrial processes. These gases may have substantially different compositions than typical syngas, and may be essentially pure hydrogen or essentially pure carbon monoxide. The gas substrate may be obtained directly from gasification or from petroleum and petrochemical processing or industrial processes or may be obtained by blending two or more streams. Also, the gas substrate may be treated to remove or alter the composition including, but not limited to, removing components by chemical or physical sorption, membrane separation, and selective reaction.

Oxygenated Compounds and Microorganisms

The oxygenated organic compounds produced by the processes of this invention will depend upon the microorganism or combination of microorganisms used for the fermentation and the conditions of the fermentation. Bioconversions of CO and $H_2/CO_2$ to acetic acid, n-butanol, butyric acid, ethanol and other products are well known. For example, a concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds. Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. Published Patent Application 20070275447, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 described in U.S. Pat. No. 8,143,037.

Mixed cultures of anaerobic microorganisms useful for the bioconversions of syngas to oxygenated organic compounds as has been discussed above. The mixed cultures can be syntrophic and involve C1-fixing microorganisms and microorganisms that bioconvert the products to the C1-fixing microorganisms to higher oxygenated organic compounds. C1-fixing microorganisms include, without limitation, homoacetogens such as *Clostridium ljungdahlii*, *Clostridium autoethanogenum*, *Clostridium ragsdalei*, and *Clostridium coskatii*. Additional C1-fixing microorganisms include *Alkalibaculum bacchi*, *Clostridium thermoaceticum*, and *Clostridium aceticum*.

For instance, Enzien, et al., in United States Published Patent Application 20140206052 A1 disclose methods for producing butanol using C1-fixing homoacetogenic microorganisms and C4-producing butyrogens. See also, Datta, et al., United States Published Patent Application 20140206066 A1. Suitable butyrogens include any microorganisms that contain either or both of the BuCoAAT pathway and BuK pathway and can grow on acetate and ethanol or on acetate and hydrogen as typically found in syngas. Butyrogens known to grow exclusively on ethanol, acetate or syngas include *Clostridium kluyveri*, *Clostridium carboxidivorans*, and *Butyribacterium methylotrophicum*.

Syntrophic C3-producing microorganisms capable of growing on ethanol and/or acetate as their primary carbon source include, but are not limited to, *Pelobacter propionicus*, *Clostridium neopropionicum*, *Clostridium propionicum*, *Desulfobulbus propionicus*, *Syntrophobacter wolinii*, *Syntrophobacter pfennigii*, *Syntrophobacter fumaroxidans*, *Syntrophobacter sulfatireducens*, *Smithella propionica*, *Desulfotomaculum thennobenzoicum* subspecies *thermosymbioticum*, *Pelotomaculum thermopropionicum*, and *Pelotomaculum schinkii*.

Fermentation Broth and Fermentation Conditions

The aqueous fermentation broth will comprise an aqueous suspension of microorganisms and various media supplements. Suitable microorganisms generally live and grow under anaerobic conditions, meaning that dissolved oxygen is essentially absent from the fermentation broth. The various adjuvants to the aqueous fermentation broth may comprise buffering agents, trace metals, vitamins, salts etc. Adjustments in the fermentation broth may induce different conditions at different times such as growth and non-growth conditions which will affect the productivity of the microorganisms. U.S. Pat. No. 7,704,723 discloses the conditions and contents of suitable aqueous fermentation broth for bioconversion CO and $H_2/CO_2$ using anaerobic microorganisms.

The aqueous menstruum is maintained under anaerobic fermentation conditions including a suitable temperature, say, between 25° C. and 60° C., frequently in the range of about 30° to 40° C. The conditions of fermentation, including the density of microorganisms and aqueous fermentation menstruum composition are preferably sufficient to achieve the sought conversion efficiency of hydrogen and carbon monoxide. The pH of the aqueous menstruum is acidic, often less than about 6.5, say, between about 4 or 4.5 and 6.0, and most frequently between about 4.5 and 5.5.

Especially where the sought oxygenated organic compound product is one or more alcohols, the electron to carbon ratio of the gas substrate is preferably in the range of about 5.5:1 to 6.5:1, say, about 5.7:1 to 6.2:1. The carbon monoxide to hydrogen mole ratio is often below about 1.1:1, say, about 0:1 to 1:1. The rate of supply of the feed gas under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous fermentation broth and the fermentation conditions. As the rate of transfer of carbon monoxide and hydrogen to the aqueous fermentation broth is a parameter for operation, conditions affecting the rate of transfer such as interfacial surface area between the gas and liquid phases and driving forces are important. Preferably the feed gas is introduced into the bioreactor in the form of microbubbles. Often the microbubbles have diameters in the range of 0.01 to 0.5, preferably 0.02 to 0.3 millimeter.

The fermentation conditions are preferably sufficient to effect at least about 85, preferably at least about 90, mole percent of the total hydrogen and carbon monoxide in the substrate gas fed to the bioreactor assembly to oxygenated organic compounds. As stated above, a combination of bubble size and duration of contact with the fermentation broth are necessary to achieve these high conversions. However, the ease and ability to achieve these high conversions is also dependent upon having the specified electron to carbon ratios. For commercial operations, the fermentation operation preferably provides a total molar conversion of hydrogen and carbon monoxide in the substrate gas feed in the range of at least about 93, preferably at least about 97, mole percent. If required to provide adequate contact time between the gas bubbles and the aqueous fermentation broth, more than one bioreactor may be used in gas flow series in the bioreactor assembly. The use of sequential, deep tank bubble column bioreactors is disclosed in United States Published Patent Application 20130078688.

Bioreactors and Assemblies

The bioreactor assembly may comprise one or more bioreactors which may be, with respect to gas flow, in parallel or in series flow. Each bioreactor may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors including, but not limited to membrane bioreactors; and static mixer reactors including, but not limited to, pipe reactors. Because of economy of capital cost and operation, deep tank bioreactors are preferred. Regardless of the type of deep tank bioreactor, especially where using microbubbles that promote a stable dispersion of bubbles in the aqueous broth, mixing currents exist that not only assure the relatively uniform aqueous phase composition but also increase the contact time between the gas bubbles and the aqueous broth.

Off-Gas (Substrate Depleted Gas) Phase

The substrate depleted gas phase egressing from the aqueous fermentation broth will contain a small fraction of the hydrogen and carbon oxides introduced into the bioreactor assembly as the feed gas. Inerts such as nitrogen and primarily methane will comprise a portion of the depleted gas phase where syngas from steam reforming or oxygen-fed, autothermal reforming, especially steam or autothermal reforming of methane-containing gas, is used. The depleted gas phase may also contain sulfur-containing compounds, alcohol and the like volatilized from the aqueous fermentation broth.

Product Recovery

The bioreactor may have added from time to time or continuously one or more streams of water, nutrients or adjuvants, and microorganisms. A portion of the aqueous fermentation broth is withdrawn from time to time or continuously from the bioreactor for product recovery. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679 shows an arrangement for a product recovery bioreactor that recovers an ethanol product from a bioreactor.

Sulfur Nutrient and Recovery

A sulfur nutrient is required by the microorganisms for the bioconversion. The processes of this invention can use any suitable sulfur nutrient as the fresh feed. Sulfur nutrients include, but are not limited to, organic compounds capable of being metabolized to yield sulfur moieties required by the microorganisms such as cysteine and inorganic sources such as hydrogen sulfide, and sulfite, bisulfite, thiosulfate and metabisulfite anions. It is believed that sulfhydryl anion is the species metabolizable by the microorganisms. The acidic pH conditions for the bioconversion provide an equilibrium favoring hydrogen sulfide, which passes from the fermentation menstruum as a component of the off-gas, as opposed to sulfhydryl anion.

The off-gas from the fermentation contains hydrogen sulfide as well as other components such as unreacted hydrogen, carbon monoxide and carbon dioxide and usually inert gases such as nitrogen and methane. The concentration of hydrogen sulfide in the off-gas is not critical to the broad aspects of this invention. The concentration will, among other things, depend on the volume of unreacted substrate and the total rate of sulfur nutrient and hydrogen sulfide passed to the aqueous fermentation menstruum. Often the concentration of hydrogen sulfide is in the range of about 100 to 10,000, say, 200 to 5000, parts per million by volume.

The off-gas is contacted with basic, aqueous solution under conditions sufficient to reduce the concentration of hydrogen sulfide. The hydrogen sulfide concentration is frequently reduced by at least about 50, and sometimes at least about 75, percent. The treated off-gas preferably has a hydrogen sulfide concentration of less than about 150, more preferably less than about 50, parts per million by volume with the pH of the basic, aqueous solution being a significant factor in defining the equilibrium between hydrogen sulfide and dissolved sulfhydryl anion. Often the temperature of the contacting is in the range of between about 10° C. to 50° C. In general lower temperatures are preferred due to increased solubility of hydrogen sulfide. The pressure of the off-gas prior to contact with the basic, aqueous solution can also vary widely. Typically the pressure is that available under the process design and thus usually is in the range of from about 100 to 1000 kPa absolute. The relative flow rates of the off-gas and the basic, aqueous solution can also vary widely. Due to the low concentration of hydrogen sulfide in the off-gas, relatively little basic, aqueous solution will be required depending upon the efficiency of the contacting and the pH of the basic, aqueous solution. Where it is desired to remove carbon dioxide from the off-gas, higher relative volumes of basic, aqueous solution may be beneficial. Sometimes the flow rate of the basic, aqueous solution to off-gas is in the range of between about 0.1 to 100, say, 1 to 50 liters per Normal cubic meter of off-gas. The duration of the contact will depend upon the other conditions of the contacting, the type of apparatus used for the contacting and the sought removal of hydrogen sulfide and, where desired, carbon dioxide. Generally the contacting is for a duration of at least about 0.1 minute, say, between about 0.1 and 60 minutes.

Any suitable unit operation can be used for the contact between the off-gas and the basic, aqueous solution. The liquid phase may be the continuous phase, but usually the off-gas is the continuous phase to reduce pressure drop. Examples of unit operations include, but are not limited to, bubble column scrubbers, venturi scrubbers, ejector venture scrubbers, vortex scrubbers, spray tower scrubbers, and packed tower scrubbers containing one or more of trays and structured packing. One or more contacting unit operations can be used, and one or more stages can be used. The contacting between the off-gas and the basic, aqueous solution can be co-current, counter current or cross-current.

A portion of the basic, aqueous solution can be recycled, if desired, to enhance scrubbing efficiency and to adjust the concentration of carbonate and bicarbonate anion in the basic, aqueous solution fed to be contacted with the off-gas. Both the relative volume of basic, aqueous solution to off-gas and the concentration of carbonate and bicarbonate anion affect the mass transfer rate of carbon dioxide from the off-gas to the scrubbing solution. Accordingly by varying one or both of these parameters, the portion of carbon dioxide removed and recycled to the bioreactor can be modulated.

Drawings

A general understanding of the invention and its application may be facilitated by reference to FIG. 1. FIG. 1 is a schematic depiction of an apparatus generally designated as 100 suitable for practicing processes in accordance with this invention. The invention can be operated in either continuous or batch mode. Both are described below. FIG. 1 omits minor equipment such as pumps, compressors, valves, instruments, the exchangers and other devices the placement of which and the operation thereof are well known to those practiced in chemical engineering. FIG. 1 also omits ancillary unit operations. The processes and operation of FIG. 1 will be described in the context of the recovery and production of ethanol. The process is readily adaptable to processes for making other oxygenated organic compounds such as acetic acid, propanol and butanol. Although shown for application in conjunction with a deep tank fermenter in FIG. 1, the instant invention can be used with other bioreactor designs As depicted apparatus 100 comprises bioreactor 102 containing aqueous fermentation menstruum 104. Bioreactor 102 is shown as a deep tank bubble column bioreactor with headspace 106 and syngas provided via line 108 to the lower portion of bioreactor 102. Substrate depleted gas, off-gas, is withdrawn from headspace 106 via line 110 and is directed to scrubber 112. Scrubber 112 may be of any suitable design. As shown, scrubber 112 is a countercurrent, packed column scrubber with the off-gas being introduced at a lower portion and the scrubbed gas exiting from the top via line 114. Scrubber 112 can also be a multistage scrubber. Each stage may be co-current to countercurrent. In some instances, cooling of one or more of the off-gas and the caustic solution used for the sorbing of sulfhydryl anion can be beneficial to enhance the solubility of sulfhydryl anion in the caustic solution.

Aqueous fermentation menstruum is continuously withdrawn from bioreactor 102 via line 116. Line 116 directs the aqueous fermentation menstruum to header 118. A portion of the withdrawn menstruum is passed via header 118 to heat exchanger 124. As the fermentation of syngas is exothermic, heat exchanger 124 serves to remove heat from this portion of the withdrawn menstruum which is then recycled to bioreactor 102 via line 126. The flow rate of this recycle is sufficient to maintain the desired temperature in bioreactor 102.

Returning to header 118 a yet further portion of the withdrawn menstruum is passed via line 128 to distillation assembly 130. Distillation assembly 130 is adapted to recover ethanol from the withdrawn menstruum. Product ethanol exits distillation assembly 130 via line 132 and non-condensables exit via line 134. A bottoms fraction is withdrawn from distillation assembly 130 via line 136 and is passed to solids separator 138. Solids separator 138 may be any suitable unit operation. For purposes of this discussion, solids separator 138 is a centrifuge and a solids-lean fraction is withdrawn via line 142 and a solids-rich fraction is withdrawn via line 140. The solids-rich fraction may be treated in any suitable manner for disposal such as being subjected to anaerobic digestion. Due to the temperatures used in distillation assembly 130, the solids are denatured. Line 142 directs the solids-lean fraction to header 144. At least a portion of the solids-lean fraction in header 144 is passed via line 146 to bioreactor 102 in order to conserve water in the process.

Focusing now on scrubber 112, a caustic aqueous solution is provided via line 148 to an upper portion where it is sprayed on the packing for contact with the upwardly flowing off-gas. The aqueous solution may be derived from any suitable source. As shown in FIG. 1, three potential sources of water for the aqueous solution can be used. First, an externally supplied caustic aqueous solution via line 150 can be used as the scrubbing solution. In some instances, it may be desired to provide a higher flow rate of aqueous solution or lower the pH of the aqueous solution. The aqueous solution, however, should be sufficiently basic that the desired reduction in hydrogen sulfide concentration in the off-gas is achieved.

One source of water for the scrubbing is the solids-lean fraction in header 144. The solids-lean fraction is typically acidic and will thus affect the pH of the caustic aqueous solution. A third source of water for the caustic aqueous solution is makeup water supplied via line 156. All, or a portion of, or none of, the makeup water can be used. The remaining portion of makeup water is passed to bioreactor 102 directly or indirectly from line 158.

The spent, caustic aqueous solution which contains sulfhydryl anion from the scrubbing is withdrawn from scrubber 112 via line 160. A portion of the spent, caustic solution can be recycled to scrubber 112 via line 162. The recycle enhances the removal of sulfhydryl anion and is a factor in determining the concentration of carbonate and bicarbonate anions in the caustic solution, and thus the degree of carbon dioxide removal from the off-gas. The remaining portion of the spent, caustic aqueous solution can be directly return to bioreactor 102 via line 166. Preferably, the spent, caustic aqueous solution is introduced at a lower portion of the bioreactor in order to maximize the mass transfer of sulfhydryl anion to the fermentation menstruum for metabolic used by the microorganisms. The spent, caustic aqueous solution can also be combined with the portion of the withdrawn fermentation menstruum being returned to bioreactor 102 via line 164. Although the pH of the combined streams will be higher than the pH of the aqueous fermentation menstruum, the relative flows can be adjusted to assure that the microorganisms are not unduly adversely affected. The advantages of this combination include the higher solubility of the sulfhydryl anion due to the higher pH and an ability of microorganisms in the combined stream to uptake sulfur nutrient prior to being introduced into the lower pH-aqueous fermentation menstruum.

It is claimed:

1. A continuous process for the anaerobic bioconversion of a gas substrate comprising carbon monoxide, hydrogen and carbon dioxide to an oxygenated organic compound in an aqueous menstruum containing microorganisms suitable for converting said substrate to oxygenated organic compound, comprising:
   a. continuously contacting said gas substrate with said aqueous menstruum under acidic, anaerobic fermentation conditions including the presence of sulfur nutrient to bioconvert said gas substrate to said oxygenated organic compound thereby providing an oxygenated organic compound-containing menstruum and a depleted gas phase containing hydrogen sulfide;
   b. continuously or intermittently introducing into said aqueous menstruum a basic, aqueous solution in an amount sufficient to maintain the aqueous menstruum above a pH that unduly adversely affects the microorganisms;
   c. continuously or intermittently withdrawing a portion of said aqueous menstruum for recovery of said oxygenated organic compound, said withdrawal being sufficient to maintain the oxygenated organic compound in said aqueous menstruum below a concentration that unduly adversely affects the microorganisms;
   d. continuously withdrawing the depleted gas phase from said aqueous menstruum; and
   e. continuously contacting at least a portion of the depleted gas phase withdrawn from said aqueous menstruum with at least a portion of the basic, aqueous solution prior to its introduction into said aqueous menstruum in step (b) thereby reducing the concentration of hydrogen sulfide in the depleted gas phase and providing sulfhydryl anion to the basic, aqueous solution.

2. The process of claim 1 wherein the basic, aqueous solution comprises a caustic, aqueous solution.

3. The process of claim 1 wherein the basic, aqueous solution prior to contacting the off depleted gas phase comprises at least one of makeup water and water sourced from the process.

4. The process of claim 3 wherein the withdrawn aqueous fermentation menstruum is subjected to distillation to provide an oxygenated organic compound product and a still bottoms, and at least a portion of the water sourced from the process comprises water from the still bottoms.

5. The process of claim 3 wherein water sourced from the process is used to lower the pH of the basic, aqueous solution.

6. The process of claim 1 wherein the pH of the basic, aqueous solution prior to contacting the off gas is between about 7.5 and 14.

7. The process of claim 1 wherein the pH of the basic, aqueous solution prior to contacting the depleted gas phase is between about 8 and 13.

8. The process of claim 1 wherein the off depleted gas phase after contacting the basic, aqueous solution contains less than about 150 parts per million by volume hydrogen sulfide.

9. The process of claim 1 wherein the off depleted gas phase after contacting the basic, aqueous solution contains less than about 50 parts per million by volume hydrogen sulfide.

10. The process of claim 1 wherein the basic, aqueous solution after contacting the depleted gas phase is directly introduced into a bioreactor containing the aqueous fermentation menstruum.

11. The process of claim 10 wherein a portion of the aqueous fermentation menstruum is continuously withdrawn from the bioreactor, cooled and returned to the bioreactor, and at least a portion of the basic, aqueous solution after contacting the depleted gas phase is combined with the withdrawn aqueous fermentation menstruum prior to being returned to the bioreactor.

12. The process of claim 1 wherein the depleted gas phase comprises carbon dioxide, and at least a portion of the carbon dioxide is removed during the contacting with the basic, aqueous solution.

13. The process of claim 12 wherein the withdrawn aqueous fermentation menstruum is subjected to distillation to provide an oxygenated organic compound product and a still bottoms, and the still bottoms is used, at least in part, to adjust the pH of the basic, aqueous solution.

14. The process of claim 1 wherein the basic, aqueous solution is introduced at a rate sufficient to maintain the pH of the aqueous fermentation menstruum above about 4.5.

15. The process of claim 14 wherein the pH of the aqueous fermentation menstruum is between about 4.5 and 6.

* * * * *